US010017396B1

(12) United States Patent
Thomas et al.

(10) Patent No.: US 10,017,396 B1
(45) Date of Patent: Jul. 10, 2018

(54) PHOSPHORS WITH NARROW GREEN EMISSION

(71) Applicant: EIE MATERIALS, INC., Lexington, KY (US)

(72) Inventors: Evan Thomas, Lexington, KY (US); Kristen Baroudi, Lexington, KY (US); Yong Bok Go, Lexington, KY (US); Robert Nordsell, Lexington, KY (US); Jonathan Melman, Lexington, KY (US)

(73) Assignee: EIE MATERIALS, INC., Lexington, KY (US)

( * ) Notice: Subject to any disclaimer, the term of this patent is extended or adjusted under 35 U.S.C. 154(b) by 0 days.

(21) Appl. No.: 15/591,629

(22) Filed: May 10, 2017

Related U.S. Application Data

(60) Provisional application No. 62/491,552, filed on Apr. 28, 2017.

(51) Int. Cl.
| C09K 11/84 | (2006.01) |
| C09K 11/88 | (2006.01) |
| C09K 11/80 | (2006.01) |
| C09K 11/78 | (2006.01) |
| C09K 11/62 | (2006.01) |
| C09K 11/63 | (2006.01) |
| H01L 33/50 | (2010.01) |
| C01F 17/00 | (2006.01) |
| C01F 7/76 | (2006.01) |
| H05B 33/08 | (2006.01) |

(Continued)

(52) U.S. Cl.
CPC ............ *C01F 17/0012* (2013.01); *C01F 7/76* (2013.01); *C09K 11/77* (2013.01); *C09K 11/7701* (2013.01); *C09K 11/7728* (2013.01); *C09K 11/7729* (2013.01); *H01L 33/502* (2013.01); *H05B 33/0803* (2013.01); *G01N 2021/6417* (2013.01)

(58) Field of Classification Search
CPC . C09K 11/7701; C09K 11/77; C09K 11/7729; C09K 11/7728; H01L 33/502
See application file for complete search history.

(56) References Cited

U.S. PATENT DOCUMENTS

| 3,639,254 A | 2/1972 | Peters |
| 3,801,702 A * | 4/1974 | Donohue ........... C09K 11/0822 252/301.4 S |

(Continued)

OTHER PUBLICATIONS

K.T. Le Thi, et al., "Investigation of the MS- Al2S3 systems (M = Ca, Sr, Ba) and luminescence properties of europium-doped thioaluminates", Materials Science and Engineering, B14 (1992) pp. 393-397.

(Continued)

*Primary Examiner* — C Melissa Koslow
(74) *Attorney, Agent, or Firm* — Innovation Counsel LLP

(57) ABSTRACT

A luminescent composition of matter is characterized by the formula $REM_{2+x}E_y$, where RE may be one or more Rare Earth elements (for example, Eu or Gd), M may be one or more elements selected from the group Al, Ga, B, In, Sc, Lu, and Y; E is one or more elements selected from the group S, Se, O, and Te; x is greater than zero; and y has the value that achieves charge balance in the formula assuming that E has a charge of −2.

30 Claims, 11 Drawing Sheets

(51) Int. Cl.
*C09K 11/77* (2006.01)
*G01N 21/64* (2006.01)

(56) References Cited

U.S. PATENT DOCUMENTS

| | | |
|---|---|---|
| 4,441,046 A | 4/1984 | James |
| 5,747,929 A | 5/1998 | Kato et al. |
| 6,417,019 B1 | 7/2002 | Mueller et al. |
| 6,597,108 B2 | 7/2003 | Yano et al. |
| 6,614,173 B2 | 9/2003 | Yano et al. |
| 6,627,251 B2 | 9/2003 | Yano et al. |
| 6,773,629 B2 | 8/2004 | Le Mercier et al. |
| 6,926,848 B2 | 8/2005 | Le Mercier et al. |
| 7,005,198 B2 | 2/2006 | Yano et al. |
| 7,018,565 B2 | 3/2006 | Tian et al. |
| 7,125,501 B2 | 10/2006 | Tian et al. |
| 7,368,179 B2 | 5/2008 | Tian et al. |
| 7,427,366 B2 | 9/2008 | Tian et al. |
| 7,453,195 B2 | 11/2008 | Radkov |
| 7,497,973 B2 | 3/2009 | Radkov et al. |
| 7,651,631 B2 | 1/2010 | Igarashi et al. |
| 7,768,189 B2 | 8/2010 | Radkov |
| 7,816,862 B2 | 10/2010 | Noguchi et al. |
| 8,147,717 B2 | 4/2012 | Ogawara et al. |
| 8,921,875 B2 | 12/2014 | Letoquin et al. |
| 9,219,201 B1 | 12/2015 | Todorov et al. |
| 9,243,777 B2 | 1/2016 | Donofrio et al. |
| 9,496,464 B2 | 11/2016 | Yao et al. |
| 9,530,944 B2 | 12/2016 | Jacobson et al. |
| 9,607,821 B2 | 3/2017 | Levin et al. |
| 2003/0042845 A1 | 3/2003 | Pires et al. |
| 2007/0284563 A1 | 12/2007 | Lee et al. |
| 2014/0077689 A1 | 3/2014 | Thompson et al. |
| 2014/0321099 A1 | 10/2014 | Kaide et al. |
| 2016/0009990 A1 | 1/2016 | Yoo et al. |
| 2016/0223146 A1 | 8/2016 | Vick et al. |

OTHER PUBLICATIONS

P.C. Donohue, et al., "The Synthesis and Photoluminescence of MiiM2iii(S,Se)4", J. Electrochem. Soc. 1974, vol. 121, Issue 1, pp. 137-142.

A.G. Paulusz, "Efficient Mn(IV) Emission in Fluorine Coordination", J. Electrochem. Soc.: Solid-State Science and Technology, Jul. 1973, pp. 942-947.

\* cited by examiner

PHOSPHORS WITH NARROW GREEN EMISSION

CROSS REFERENCE TO RELATED APPLICATIONS

This application claims benefit of priority to U.S. Provisional Patent Application No. 62/491,552 titled "Phosphors With Narrow Green Emission" and filed Apr. 28, 2017, which is incorporated herein by reference in its entirety.

This invention was made with federal government support from the National Science Foundation under award number 1534771. The federal government has certain rights in the invention. This invention was also made with an award from the Kentucky Cabinet for Economic Development, Office of Entrepreneurship, under Grant Agreement KSTC-184-512-17-247 with the Kentucky Science and Technology Corporation.

FIELD OF THE INVENTION

The invention relates generally to phosphors having narrow green emission.

BACKGROUND

Alkaline earth thiogallate and alkaline earth thioaluminate phosphors activated with europium are known in the art for both electroluminescent systems and phosphor converted LED systems. These materials can readily absorb the emission from blue, violet, or near UV emitting light sources such as the commonplace InGaN light emitting diodes. These typically green phosphor materials can be used independently to generate a green light, or they can be combined with other phosphor materials to generate white or other colored light. Similarly, these green phosphor materials may be combined, for example, with a blue or other LED and a red phosphor in order to generate the backlighting unit for a display, such as a mobile phone, tablet, laptop, monitor, or television.

In general lighting, it is often desirable to have a broad emission spectrum to improve the color rendering index or other quality of light metrics, such as CQS or TM-30-15. However, sometimes in lighting it is desirable to provide extra light in certain wavelength regions in order to accentuate certain features; for instance, grocery store display cases for beef may include extra light in the red region of the spectrum, similarly, spinach or green papers may appear more pleasing when the lighting provides extra light in certain green wavelengths.

In display backlighting, it is more desirable to have a narrow emission wavelength so that the color (a) appears more saturated and widens the green vertex of the color gamut, and (b) sustains fewer losses when passing through the green filter of a typical LCD filter system, because the majority of its intensity is well aligned with the highest transmissivity of the filter.

SUMMARY

Phosphors of the present invention address the challenge of helping to preferentially saturate certain green regions of the emission spectrum for lighting applications and improve the green gamut point of a display backlight unit by providing a phosphor composition with a relatively narrow green emission spectrum.

DETAILED DESCRIPTION

The following detailed description should be read with reference to the drawings, which depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used in this specification and the appended claims, the singular forms "a," "an," and "the" include plural referents unless the context clearly indicates otherwise.

Figure 1:
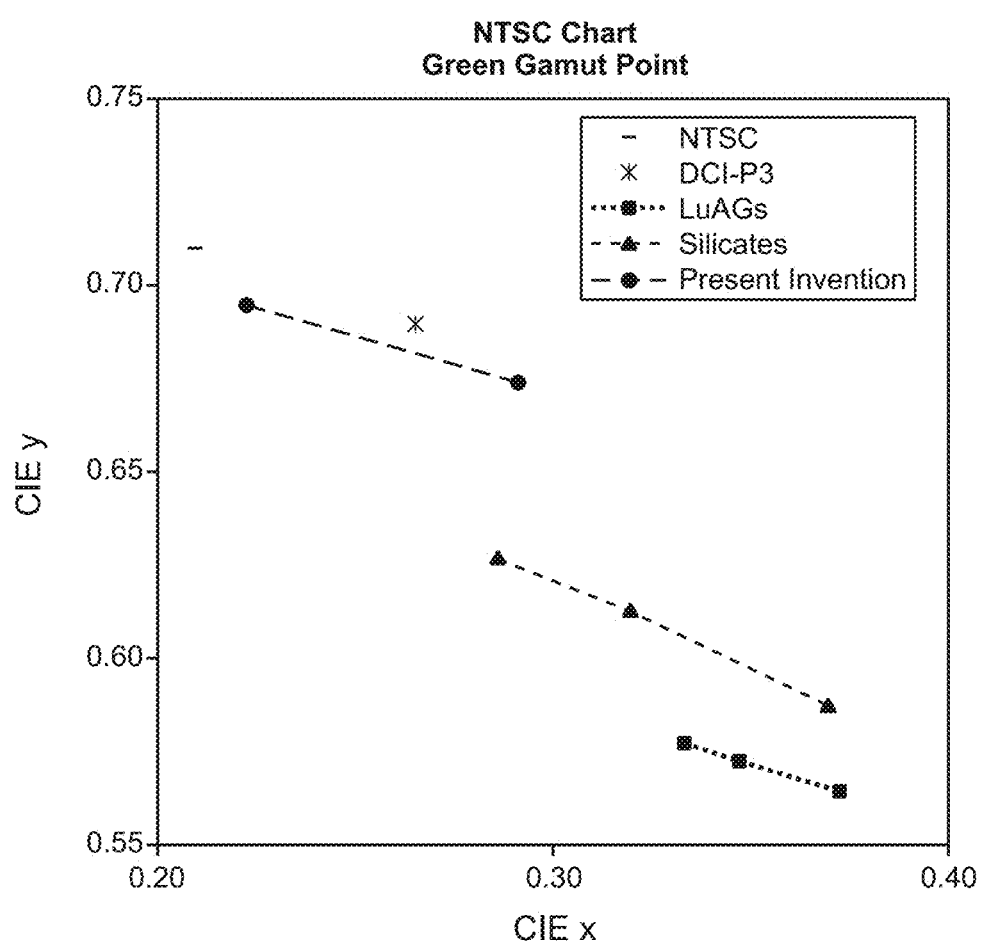
FIG. 1 is a plot showing CIE xy color points of example commercially available phosphors, the green gamut points from the NTSC color gamut and the DCI-P3 color gamut, and emission from example phosphors of the present invention peaked at 530 nm and 537 nm.

Phosphors of the present invention emit green light over a relatively narrow range of emission wavelengths in response to excitation with, for example, ultraviolet, violet, blue, or short wavelength green light. Their narrow emission may appear more saturated and widen the green vertex of the color gamut compared to commercially available green phosphors. As an example of this advantage, FIG. 1 shows the CIE xy color points of example commercially available phosphors such as LuAGs and silicates peaked at 525 nm, 530 nm, and 540 nm (such as available for example from Intematix Corporation, Fremont, Calif., under product numbers GAL525, GAL530, GAL540, EG2762, EG3261, and EG3759), the green gamut points from the NTSC color gamut and the DCI-P3 color gamut, and emission from example phosphors of the present invention peaked at 530 nm and 537 nm.

Phosphors of the present invention have the empirical composition $REM_{2+x}E_y$, where RE may be one or more Rare Earth elements (for example, Eu or Gd), M may be one or more elements selected from the group Al, Ga, B, In, Sc, Lu or Y, E may be one or more elements selected from the group S, Se, O, or Te, x is greater than zero, or greater than or equal to 0.1, or greater than or equal to 0.3, or greater than or equal to 0.7, and less than or equal to 0.9, and y has the value that achieves charge balance in the formula assuming that E has a charge of −2. (In the experimental examples described in this specification, reactions are always run with an excess of chalcogen, allowing the reaction to utilize what is needed to form the charge balanced composition). Some minor compositional substitutions may also occur from the use of reaction promoters including but not limited to $AlCl_3$ or $I_2$. The phosphors may have the same basic pseudoorthorhombic crystal structure as $REM_2E_4$ (e.g., $EuGa_2S_4$). The phosphors may comprise a mixture of a $REM_2E_4$ crystal phase and one or more binary chalcogenide crystals phases such as for example an $M_2E_3$ (e.g., $Ga_2S_3$) crystal phase or an ME (e.g., GaS) crystal phase. In some variations the composition is characterized by the formula $Eu(Al,Ga)_{2+x}S_y$, and the ratio of Al to Ga is between about 1:3 and about 2:1.

Phosphors of the present invention may show an improvement over known alkaline earth thiogallate phosphors by providing a narrower emission spectrum than is provided by state of the art thiogallate phosphors. Phosphors of the present invention may show an improvement in brightness over $EuM_2E_4$ compositions such as, for example, $EuAl_2S_4$, $EuAl_2Se_4$, and $EuGa_2S_4$ disclosed by Thi et al. *Materials Science & Engineering B*14 (1992), No 4, pp. 393-397, Donohue U.S. Pat. No. 3,801,702 (issued Apr. 2, 1974), and Donohue and Hanlon, *Journal of the Electrochemical Society: Solid-State Science and Technology* (1974), Vol. 121, No. 1, pp. 137-142.

In particular, phosphors having the empirical formula $REM_{2+x}E_y$ with x>0 described above may provide a significant increase in the relative intensity of the phosphor's emission peak, in some cases greater than two-fold, compared to phosphors having the composition $REM_2E_4$. The optimal value of x may vary with the exact composition of the system. However, x=0.7 appears to be at or near an optimal value for many choices of M, such as for example for RE=Eu and M=1/3 Al, 2/3 Ga.

Phosphors of the present invention may be tuned through a wavelength range based upon application requirements by varying the M and E components of the composition. For example, for phosphors having the empirical formula $Eu(Al, Ga)_{2+x}(S,Se)_y$, the emission wavelength range can extend for example from a peak emission wavelength around 490 nm for $EuAl_{2+x}Se_y$, to a peak emission wavelength around 550 nm for $EuGa_{2+x}S_y$. Even longer wavelengths of emission can be obtained by incorporating indium or oxygen. For phosphors having the empirical formula $Eu(Al,Ga)_{2+x}S_y$, the peak emission wavelength may vary with percent Ga approximately as follows: 0% Ga, 505 nm; 5% Ga, 509 nm; 14% Ga, 512 nm; 25% Ga, 517 nm; 50% Ga, 527 nm; 55% Ga, 530 nm; 60% Ga, 533 nm; 65% Ga, 533 nm; 70% Ga, 535 nm; 75% Ga, 541 nm; 100% Ga, 545 nm. For phosphors having the empirical formula $Eu(Al,Ga)_{2+x}(S,Se)_y$, the percent Ga may be, for example, ≥0%, ≥5%, ≥10%, ≥15%, ≥20%, ≥25%, ≥30%, ≥35%, ≥40%, ≥45%, ≥50%, ≥55%, ≥60%, ≥65%, ≥70%, ≥75%, ≥80%, ≥85%, ≥90%, ≥95%, 0% to 5%, 5% to 10%, 10% to 15%, 15% to 20%, 20% to 25%, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90%, 90%, 95%, 95% to 100%, or 50% to 75%.

A number of fluxes/reaction promoters have been investigated, such as for example $I_2$, $AlF_3$, $AlCl_3$, $AlBr_3$, $GaCl_3$, $GaBr_3$, $BaF_2$, $EuCl_3$, $EuI_2$, and $Na_2S$. Use of promoters with cations other than those in the targeted final product (e.g., Ba and Na) resulted in the formation of alternative phases, not meeting the desired properties of the invention.

The phosphors of the present invention may be optically coupled with an excitation source in any conventional manner. One of the more common methods is to combine phosphors, such as the green phosphor disclosed here, with a red phosphor and optional blue and/or yellow phosphors. The phosphors may be combined together and then added to an encapsulant, such as silicone, epoxy, or some other polymer, or the phosphors may be combined during their addition to the encapsulant. The phosphor loaded encapsulant may then be placed in the optical path of an excitation source. One common method is to deposit the slurry of phosphor or phosphors into an LED (light emitting diode) package which contains an LED die. The slurry is then cured forming an encapsulated LED package. Other methods include forming the encapsulant into a shape or coating the encapsulant onto a substrate which may already be in a particular shape, or may be subsequently formed into a particular shape. Additionally, the phosphor containing encapsulant may be coated on the in-coupling region of a light guide, or on the out-coupling region of a light guide, such as a light guide intended for use in a display. The combination of an excitation source and the phosphors of the present invention may be used in general lighting, niche lighting applications, display backlighting, or other lighting applications.

Applicant has prepared and characterized a number of example phosphor samples having the empirical composition $REM_{2+x}E_y$ described above. Preparation and characterization of these examples is described below and summarized in Table 1. For some samples one or more crystal phases observed by powder x-ray diffraction are reported in addition to the empirical composition. Emission spectra were measured using a Fluorolog-3 spectrofluorometer with xenon lamp or an Ocean Optics spectrometer used in conjunction with an external blue or violet LED excitation source. Excitation spectra were measured using a Fluorolog-3 spectrofluorometer with xenon lamp. Powder x-ray diffraction spectra were measured using a Rigaku MiniFlex600.

Example 1 $EuAl_{2.133}B_{0.567}S_{5.05}$ (Sample Number KB3-063-406), x=0.7

A 1:2.133:0.567:4.4 ratio of Eu:Al:B:S was ground in an argon filled glovebox and sealed in a fused silica tube. The sample was heated at 400° C. for 6 hours, then the temperature was increased and held at 800° C. for 12 hours. The sample was cooled to room temperature at about 130° C./hour. The sample was opened in an argon filled glovebox, ground with an additional 10 wt % sulfur and sealed in a fused silica tube and heated a second time with the same heating profile.

Figure 2A:
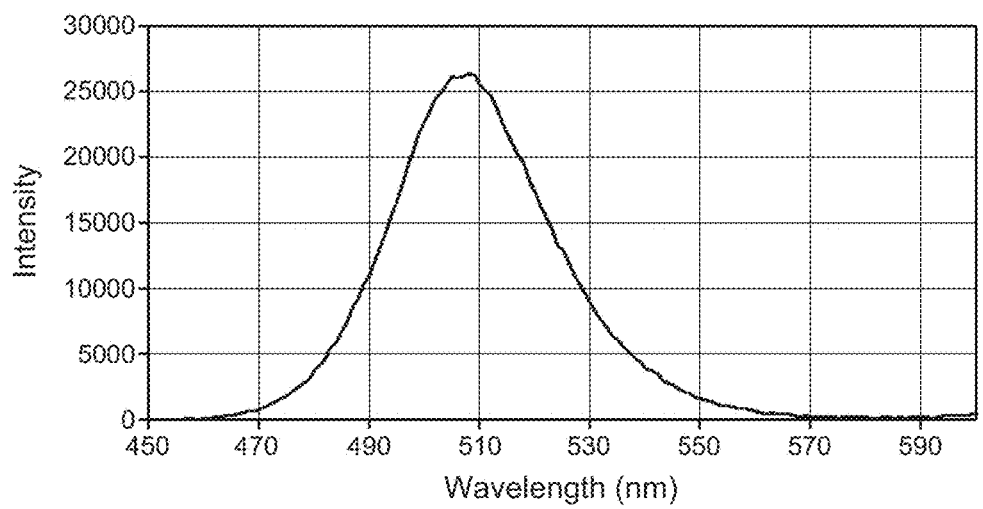
FIGS. 2A-2C show, respectively, an emission spectrum, an excitation spectrum, and a powder x-ray diffraction pattern for $EuAl_{2.133}B_{0.567}S_{5.05}$.
Figure 2B:
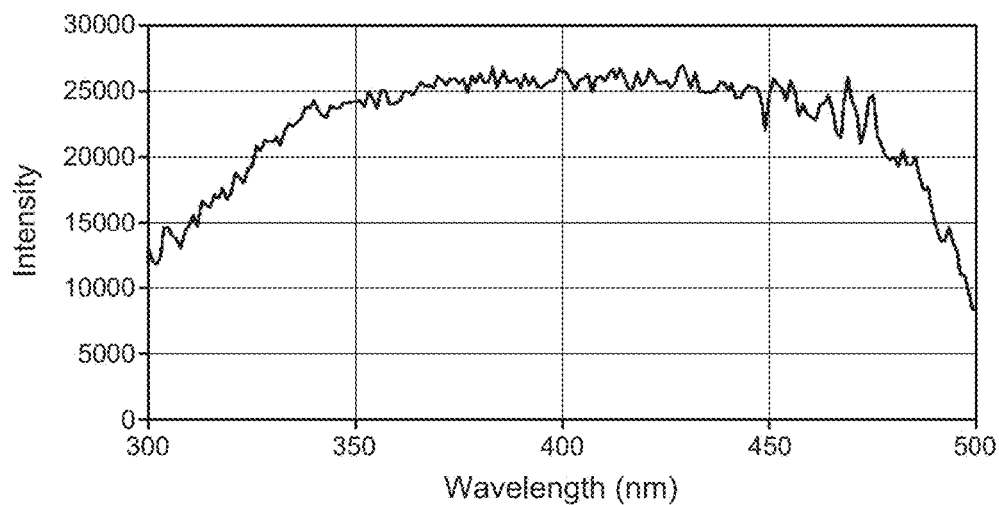
Figure 2C:
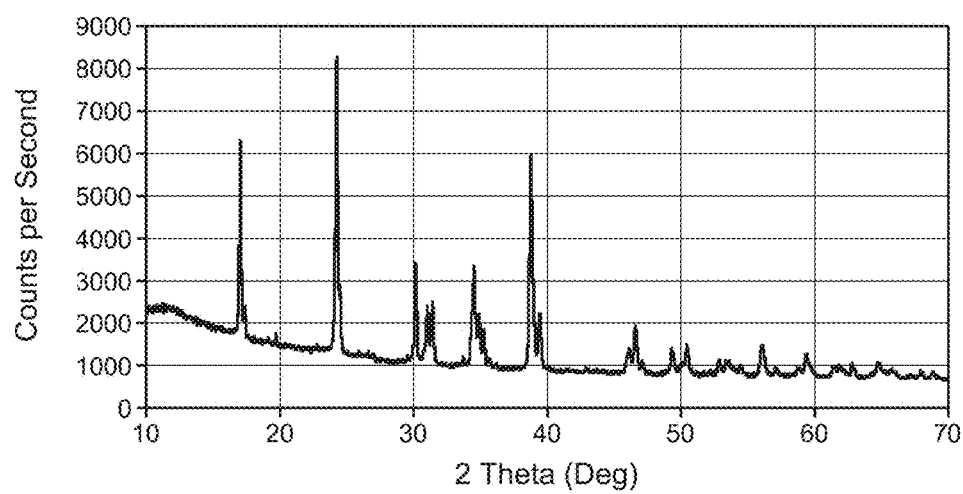

FIG. 2A shows an emission spectrum from this sample with excitation at 395 nm. FIG. 2B shows an excitation spectrum for this sample with emission detected at 510 nm. FIG. 2C shows a powder x-ray diffraction (XRD) measurement for this sample, which matches the XRD pattern for $EuAl_2S_4$ (standard PDF #01-081-2821). This suggests that some of the excess Al, excess B, and excess S may be present in one or more a binary chalcogenide phases.

Example 2 $EuAl_{2.322}Lu_{0.378}S_{5.05}$ (Sample Number KB3-059-399), x=0.7

A 1:2.322:0.378:4.4 ratio of Eu:Al:Lu:S was ground in an argon filled glovebox and sealed in a fused silica tube. The sample was heated at 400° C. for 6 hours, then the temperature was increased and held at 800° C. for 12 hours. The sample was cooled to room temperature at about 130° C./hour. The sample was opened in an argon filled glovebox, ground with an additional 10 wt % sulfur and sealed in a fused silica tube and heated a second time with the same heating profile.

Figure 3A:
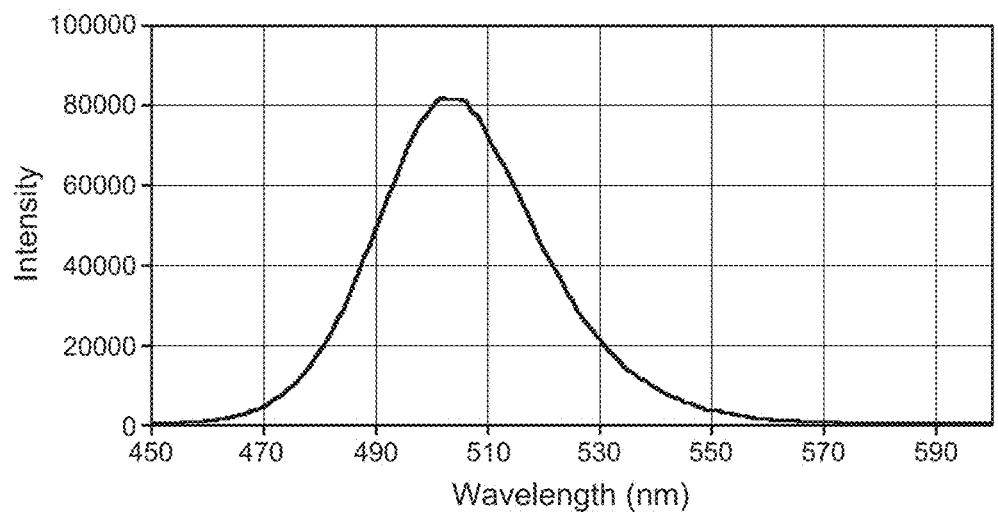
FIGS. 3A-3B show, respectively, an emission spectrum and an excitation spectrum for $EuAl_{2.322}Lu_{0.378}S_{5.05}$.
Figure 3B:
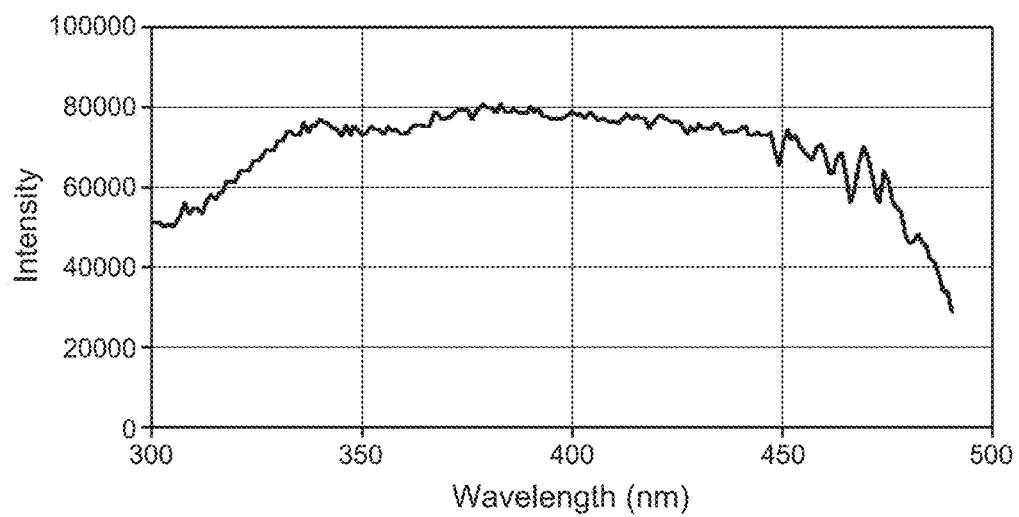

FIG. 3A shows an emission spectrum from this sample with excitation at 395 nm. FIG. 3B shows an excitation spectrum for this sample with emission detected at 505 nm.

Example 3 $EuAl_{0.8}Ga_{1.2}S_4$, (Sample Number KB3-125-488), x=0, Comparative Example Eu, $Al_2S_3$, $Ga_2S_3$, and S were mixed in a stoichiometric ratio and an additional 0.25 sulfur per formula unit and 7.5 wt % $AlCl_3$ were added (0.116 g Eu, 0.046 g $Al_2S_3$, 0.108 g $Ga_2S_3$, 0.031 g S, 0.023 g $AlCl_3$). The mixture was ground in an argon filled glovebox and sealed in a fused silica tube. The samples were heated at 400° C. for 1 hour, then the temperature was increased and held at 900° C. for 6 hours. The sample was cooled to room temperature at 50° C./hour.

Figure 4A:
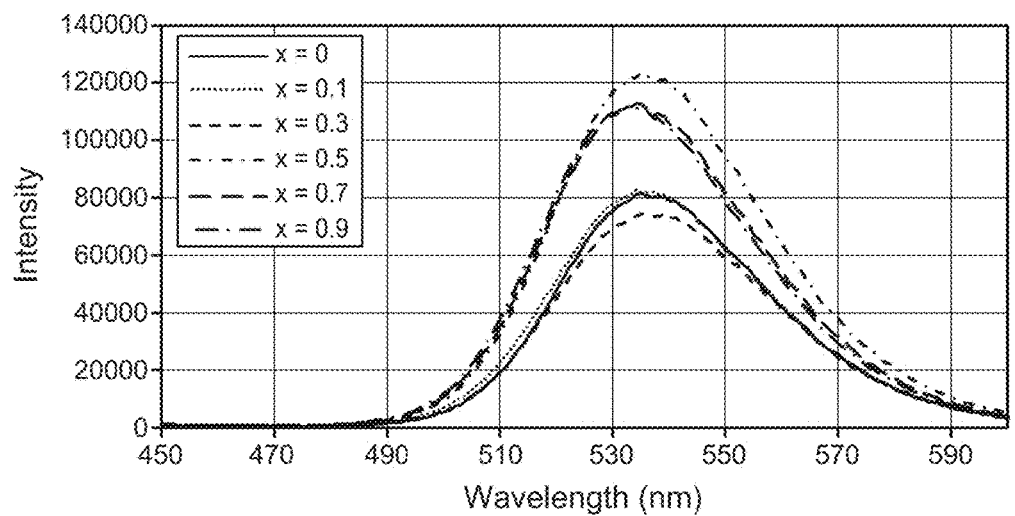
FIGS. 4A-4C show, respectively, emission spectra, excitation spectra, and powder x-ray diffraction patterns for $Eu(Al_{0.4}Ga_{0.6})_{2+x}S_y$, with x=0, 0.1, 0.3, 0.5, 0.7, and 0.9.
Figure 4B:
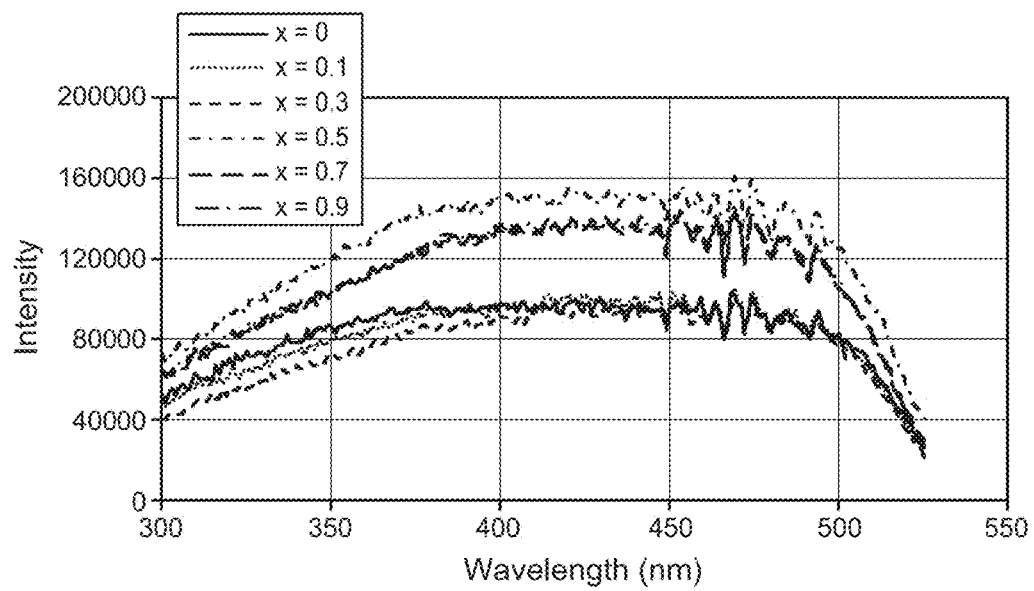
Figure 4C:
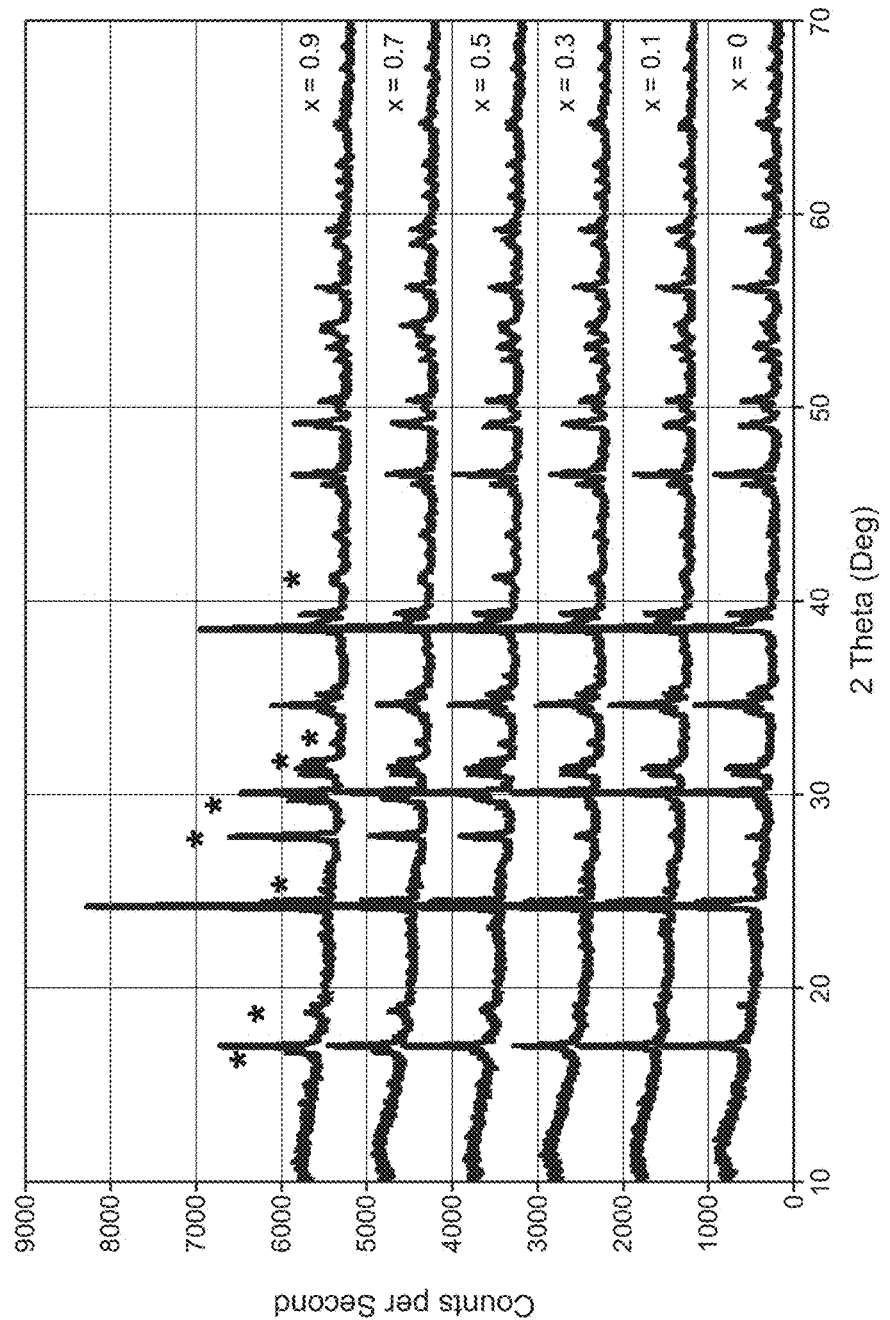

FIG. 4A shows the emission spectrum for this sample (labeled x=0) with excitation at 395 nm. FIG. 4B shows the excitation spectrum for this sample (labeled x=0) with emission detected at 535 nm. FIG. 4C shows a powder x-ray diffraction (XRD) measurement for this sample, labeled x=0.

Example 4 $EuAl_{0.84}Ga_{1.26}S_{4.15}$, (Sample Number KB3-125-489), x=0.1

Eu, $Al_2S_3$, $Ga_2S_3$, and S were mixed in a stoichiometric ratio and an additional 0.25 sulfur per formula unit and 7.5 wt % $AlCl_3$ were added (0.113 g Eu, 0.047 g $Al_2S_3$, 0.110 g $Ga_2S_3$, 0.030 g S, 0.023 g $AlCl_3$). The mixture was ground in an argon filled glovebox and sealed in a fused silica tube. The samples were heated at 400° C. for 1 hour, then the temperature was increased and held at 900° C. for 6 hours. The sample was cooled to room temperature at 50° C./hour.

FIG. 4A shows the emission spectrum for this sample (labeled x=0.1) with excitation at 395 nm. FIG. 4B shows the excitation spectrum for this sample (labeled x=0.1) with emission detected at 535 nm. FIG. 4C shows a powder x-ray diffraction (XRD) measurement for this sample, labeled x=0.1.

Example 5 $EuAl_{0.02}Ga_{1.38}S_{4.45}$, (Sample Number KB3-125-490), x=0.3

Eu, $Al_2S_3$, $Ga_2S_3$, and S were mixed in a stoichiometric ratio, and an additional 0.25 sulfur per formula unit and 7.5 wt % $AlCl_3$ were added (0.108 g Eu, 0.049 g, $Al_2S_3$, 0.115 g $Ga_2S_3$, 0.028 g S, 0.023 g $AlCl_3$). The mixture was ground in an argon filled glovebox and sealed in a fused silica tube. The samples were heated at 400° C. for 1 hour, then the temperature was increased and held at 900° C. for 6 hours. The sample was cooled to room temperature at 50° C./hour.

FIG. 4A shows the emission spectrum for this sample (labeled x=0.3) with excitation at 395 nm. FIG. 4B shows the excitation spectrum for this sample (labeled x=0.3) with emission detected at 535 nm. FIG. 4C shows a powder x-ray diffraction (XRD) measurement for this sample, labeled x=0.3.

Example 6 $EuAlGa_{1.5}S_{4.75}$, (Sample Number KB3-125-491), x=0.5

Eu, $Al_2S_3$, $Ga_2S_3$, and S were mixed in a stoichiometric ratio, and an additional 0.25 sulfur per formula unit and 7.5 wt % $AlCl_3$ were added (0.103 g Eu, 0.051 g $Al_2S_3$, 0.120 g $Ga_2S_3$, 0.027 g S, 0.023 g $AlCl_3$). The mixture was ground in an argon filled glovebox and sealed in a fused silica tube. The samples were heated at 400° C. for 1 hour, then the temperature was increased and held at 900° C. for 6 hours. The sample was cooled to room temperature at 50° C./hour.

FIG. 4A shows the emission spectrum for this sample (labeled x=0.5) with excitation at 395 nm. FIG. 4B shows the excitation spectrum for this sample (labeled x=0.5) with emission detected at 535 nm. FIG. 4C shows a powder x-ray diffraction (XRD) measurement for this sample, labeled x=0.5.

Example 7 $EuAl_{1.08}Ga_{1.62}S_{5.05}$, (Sample Number KB3-126-492), x=0.7

Eu, $Al_2S_3$, $Ga_2S_3$, and S were mixed in a stoichiometric ratio, and an additional 0.25 sulfur per formula unit and 7.5 wt % $AlCl_3$ were added (0.098 g Eu, 0.052 g $Al_2S_3$, 0.124 g $Ga_2S_3$, 0.026 g S, 0.023 g $AlCl_3$). The mixture was ground in an argon filled glovebox and sealed in a fused silica tube. The samples were heated at 400° C. for 1 hour, then the temperature was increased and held at 900° C. for 6 hours. The sample was cooled to room temperature at 50° C./hour.

FIG. 4A shows the emission spectrum for this sample (labeled x=0.7) with excitation at 395 nm. FIG. 4B shows the excitation spectrum for this sample (labeled x=0.7) with emission detected at 535 nm. FIG. 4C shows a powder x-ray diffraction (XRD) measurement for this sample, labeled x=0.7.

Example 8 $EuAl_{1.16}Ga_{1.74}S_{5.35}$ (Sample Number KB3-126-493), x=0.9

Eu, $Al_2S_3$, $Ga_2S_3$, and S, were mixed in a stoichiometric ratio and an additional 0.25 sulfur per formula unit and 7.5 wt % $AlCl_3$ were added (0.094 g Eu, 0.054 g $Al_2S_3$, 0.127 g $Ga_2S_3$, 0.025 g S, 0.023 g $AlCl_3$). The mixture was ground in an argon filled glovebox and sealed in a fused silica tube. The samples were heated at 400° C. for 1 hour, then the temperature was increased and held at 900° C. for 6 hours. The sample was cooled to room temperature at 50° C./hour.

FIG. 4A shows the emission spectrum for this sample (labeled x=0.9) with excitation at 395 nm. FIG. 4B shows the excitation spectrum for this sample (labeled x=0.9) with emission detected at 535 nm. FIG. 4C shows a powder x-ray diffraction (XRD) measurement for this sample, labeled x=0.9.

XRD Data for Examples 3-8

In FIG. 4C the major phase in each XRD pattern matches $EuGa_2S_4$ (standard PDF#01-071-0588). $Ga_2S_3$ (PDF #00-054-0415) is also present (peaks are marked with stars), and the amount increases as "x" increases. The peaks for both phases are shifted to slightly higher angle than the database patterns, likely due to incorporation of aluminum.

Example 9 EuAl$_{1.08}$Ga$_{1.62}$S$_{5.05}$ (Sample Number KB3-132-506), x=0.7

This sample was prepared using an AlF$_3$ flux, rather than an AlCl$_3$ flux as in example 7. Eu, Al$_2$S$_3$, Ga$_2$S$_3$, and S, were mixed in a stoichiometric ratio. An additional 0.25 sulfur per formula unit and 7.5 wt % AlF$_3$ were added. The mixture was ground in an argon filled glovebox and sealed in a carbon coated fused silica tube. The samples were heated at 400° C. for 1 hour, then the temperature was increased and held at 800° C. for 6 hours. The samples were cooled to room temperature at 50° C./hour.

Example 10 EuAl$_{0.8}$Ga$_{1.2}$S$_4$ (Sample Number KB3-133-507), x=0

This sample was prepared using an AlF$_3$ flux, rather than an AlCl$_3$ flux as in example 3. Eu, Al$_2$S$_3$, Ga$_2$S$_3$, and S, were mixed in a stoichiometric ratio. An additional 0.25 sulfur per formula unit and 7.5 wt % AlF$_3$ were added. The mixture was ground in an argon filled glovebox and sealed in a carbon coated fused silica tube. The samples were heated at 400° C. for 1 hour, then the temperature was increased and held at 800° C. for 6 hours. The samples were cooled to room temperature at 50° C./hour.

Example 11 EuAl$_2$Se$_4$, (Sample Number YBG-170419-1), x=0, Comparative Example Stoichiometric amounts of Eu, Al, and Se were thoroughly ground in a mortar with a pestle in the glove box. The mixture was placed in dried, carbon coated silica tubes, which were evacuated and sealed at a length of about 5 in. The reaction was carried out in a box furnace. The temperature was raised to 400° C. and held for 6 hours and raised again to 800° C. and held for 6 hours, then cooled to room temperature for 6 hours.

Figure 5A:
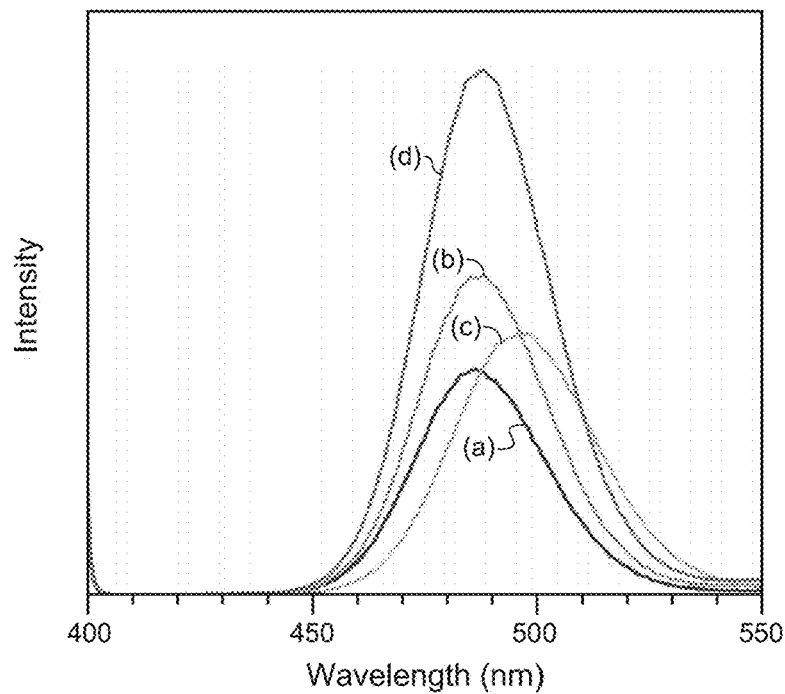
FIGS. 5A-5B show, respectively, emission spectra and excitation spectra for $EuAl_2Se_4$, $EuAl_{2.4}Se_{4-6}$, $EuAl_{2.4}Se_{3.6}S$, and $EuAl_{2.7}Se_{5.05}$.
Figure 5B:
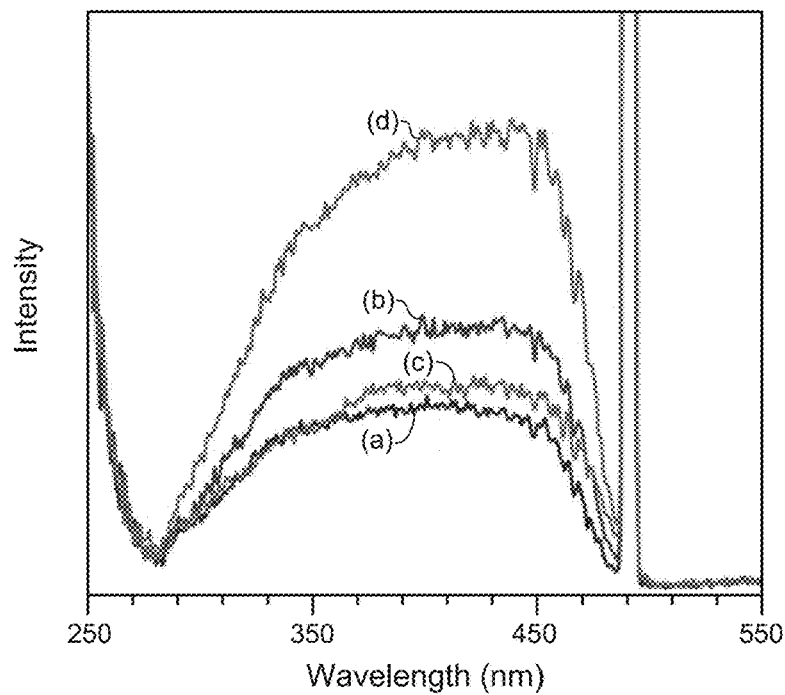

FIG. 5A shows the emission spectrum for this sample (labeled "a") for excitation at 395 nm. The relative intensity of the emission peak is 100% compared to the other emission spectra in this figure. FIG. 5B shows the excitation spectrum for this sample (labeled "a") with emission detected at 490 nm.

Example 12 EuAl$_{2.4}$Se$_{4.6}$ (Sample Number YBG-170419-2), x=0.4

Stoichiometric amounts of Eu, Al, and Se were thoroughly ground in a mortar with a pestle in the glove box. The mixture was placed in dried, carbon coated silica tubes, which were evacuated and sealed at a length of about 5 in. The reaction was carried out in a box furnace. The temperature was raised to 400° C. and held for 6 hours and raised again to 800° C. and held for 6 hours, then cooled to room temperature for 6 hours.

FIG. 5A shows the emission spectrum for this sample (labeled "b") for excitation at 395 nm. The relative intensity of the emission peak is 144% compared to the other emission spectra in this figure. FIG. 5B shows the excitation spectrum for this sample (labeled "b") with emission detected at 490 nm.

Example 13 EuAl$_{2.4}$Se$_{3.6}$S (Sample Number YBG-170419-4), x=0.4

Stoichiometric amounts of Eu, Al, Se, and S were thoroughly ground in a mortar with a pestle in the glove box. The mixture was placed in dried, carbon coated silica tubes, which were evacuated and sealed at a length of about 5 in. The reaction was carried out in a box furnace. The temperature was raised to 400° C. and held for 6 hours and raised again to 800° C. and held for 6 hours, then cooled to room temperature for 6 hours.

FIG. 5A shows the emission spectrum for this sample (labeled "c") for excitation at 395 nm. The relative intensity of the emission peak is 117% compared to the other emission spectra in this figure. FIG. 5B shows the excitation spectrum for this sample (labeled "c") with emission detected at 490 nm.

Example 14 EuAl$_{2.7}$Se$_{5.05}$ (Sample Number YBG-170419-5), x=0.7

Stoichiometric amounts of Eu, Al, and Se were thoroughly ground in a mortar with a pestle in the glove box. The mixture was placed in dried, carbon coated silica tubes, which were evacuated and sealed at a length of about 5 in. The reaction was carried out in a box furnace. The temperature was raised to 400° C. and held for 6 hours and raised again to 800° C. and held for 6 hours, then cooled to room temperature for 6 hours.

FIG. 5A shows the emission spectrum for this sample (labeled "d") for excitation at 395 nm. The relative intensity of the emission peak is 224% compared to the other emission spectra in this figure. FIG. 5B shows the excitation spectrum for this sample (labeled "d") with emission detected at 490 nm.

Example 15 EuAl$_{2.07}$In$_{0.23}$S$_{4.45}$ (Sample Number KB3-132-503)

Eu, Al$_2$S$_3$, In$_2$S$_3$, and S were mixed in a stoichiometric ratio. The mixtures were ground in an argon filled glovebox and sealed in a fused silica tube. The samples were heated at 400° C. for 1 hour, then the temperature was increased and held at 900° C. for 6 hours. The samples were cooled to room temperature at 50° C./hour.

Figure 6:
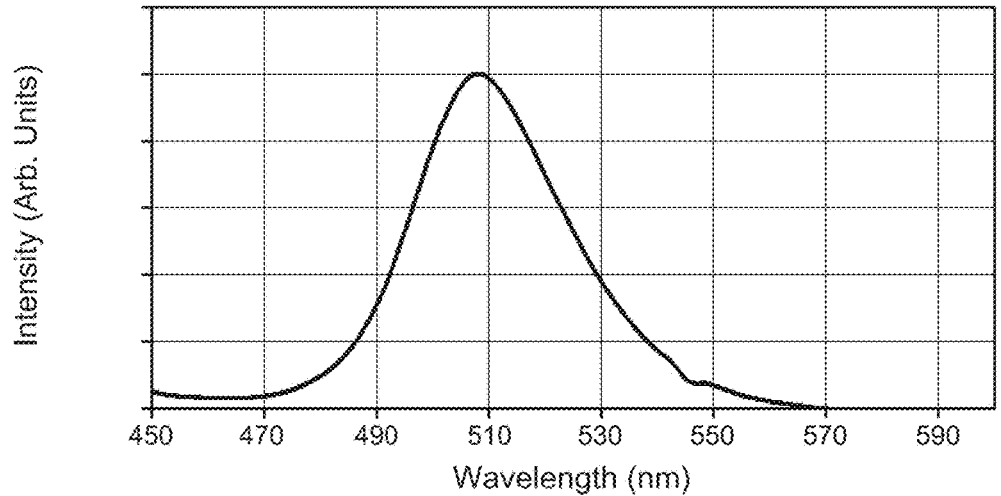
FIG. 6 shows an emission spectrum for $EuAl_{2.07}In_{0.23}S_{4.45}$.

FIG. 6 shows the emission spectrum for this sample for excitation at 405 nm.

Example 16 EuAl$_{1.84}$In$_{0.46}$S$_{4.45}$ (Sample Number KB3-132-504)

Eu, Al$_2$S$_3$, In$_2$S$_3$, and S were mixed in a stoichiometric ratio. The mixtures were ground in an argon filled glovebox and sealed in a fused silica tube. The samples were heated at 400° C. for 1 hour, then the temperature was increased and held at 900° C. for 6 hours. The samples were cooled to room temperature at 50° C./hour.

Figure 7:
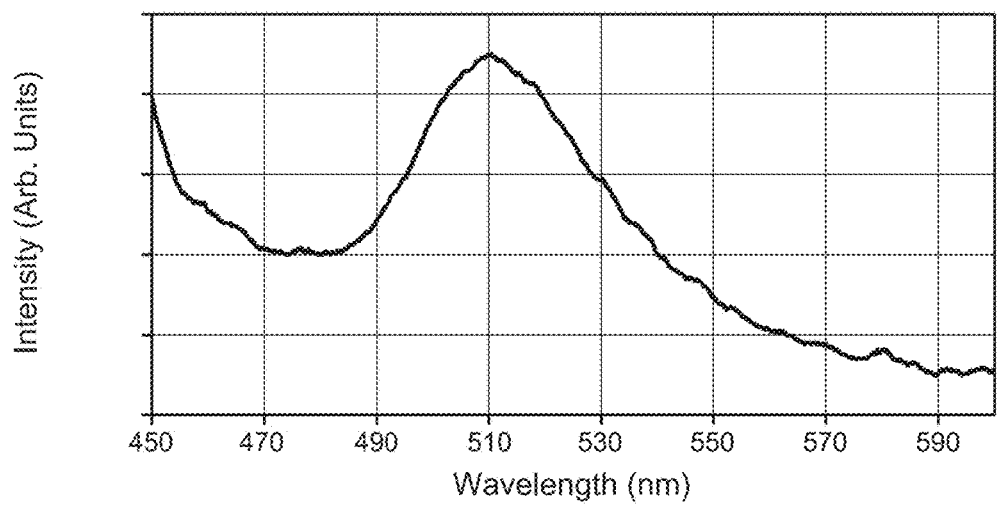
FIG. 7 shows an emission spectrum for $EuAl_{1.84}In_{0.46}S_{4.45}$.

FIG. 7 shows the emission spectrum for this sample for excitation at 405 nm.

Example 17 EuAl$_{1.61}$Ga$_{0.23}$In$_{0.46}$S$_{445}$ (Sample Number KB3-132-505)

Eu, Al$_2$S$_3$, Ga$_2$S$_3$, In$_2$S$_3$, and S were mixed in a stoichiometric ratio. The mixtures were ground in an argon filled glovebox and sealed in a fused silica tube. The samples were heated at 400° C. for 1 hour, then the temperature was increased and held at 900° C. for 6 hours. The samples were cooled to room temperature at 50° C./hour.

Figure 8:
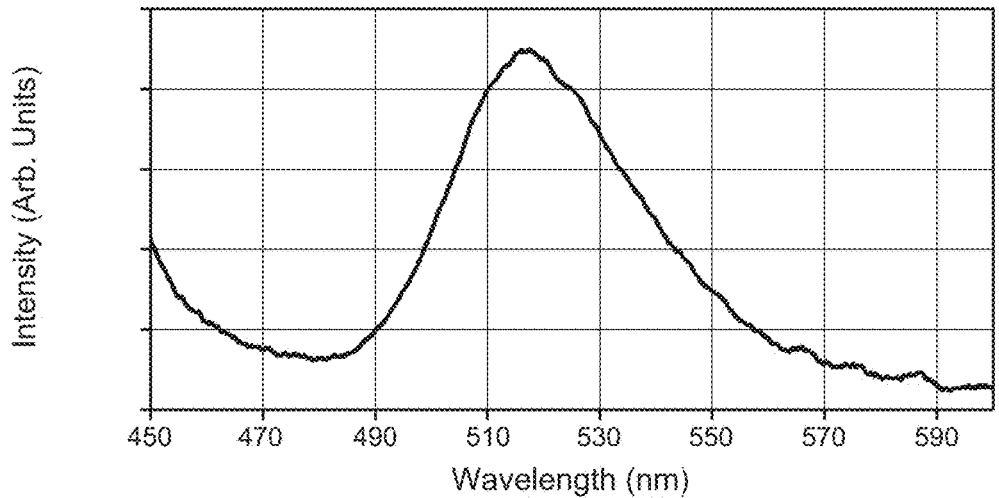
FIG. 8 shows an emission spectrum for $EuAl_{1.61}Ga_{0.23}In_{0.46}S_{4.45}$.

FIG. 8 shows the emission spectrum for this sample for excitation at 405 nm.

Example 18 EuAlGa$_{1.5}$S$_{4.75}$ (Sample Number ELTAlS-056A)

A 1.2 g mixture of stoichiometric amounts of Eu, Al$_2$S$_3$, Ga$_2$S$_3$ and S was prepared under Ar. The mixture was combined with 20 wt % excess S, and separated into five 200 mg portions for use in this example and in examples 19-22. For this example one 200 mg portion of the mixture was thoroughly mixed with 30 mg (15 wt %) of an AlBr$_3$ flux and sealed in an evacuated quartz tube. The ampoule was heated to 400° C. over 2 hours, dwelled for 1 hour at that temperature, and then was heated to 900° C. over 1.5 hours and dwelled at that temperature for 6 h before being slowly cooled to room temperature at 50° C./hr.

Example 19 EuAlGa$_{1.5}$S$_{4.75}$ (Sample Number ELTAlS-056B)

A 200 mg portion of the 1.2 g mixture of stoichiometric amounts of Eu, Al$_2$S$_3$, Ga$_2$S$_3$ and S prepared in Example 18 was thoroughly mixed with 30 mg (15 wt %) of a GaBr$_3$ flux and sealed in an evacuated quartz tube. The ampoule was heated to 400° C. over 2 hours, dwelled for 1 hour at that temperature, and then was heated to 900° C. over 1.5 hours and dwelled at that temperature for 6 h before being slowly cooled to room temperature at 50° C./hr.

Example 20 EuAlGa$_{1.5}$S$_{4.75}$ (Sample Number ELTAlS-056C)

A 200 mg portion of the 1.2 g mixture of stoichiometric amounts of Eu, Al$_2$S$_3$, Ga$_2$S$_3$ and S prepared in Example 18 was thoroughly mixed with 30 mg (15 wt %) of a GaCl$_3$ flux and sealed in an evacuated quartz tube. The ampoule was heated to 400° C. over 2 hours, dwelled for 1 hour at that temperature, and then was heated to 900° C. over 1.5 hours and dwelled at that temperature for 6 h before being slowly cooled to room temperature at 50° C./hr.

Example 21 EuAlGa$_{1.5}$S$_{4.75}$ (Sample Number ELTAlS-056D)

A 200 mg portion of the 1.2 g mixture of stoichiometric amounts of Eu, Al$_2$S$_3$, Ga$_2$S$_3$ and S prepared in Example 18 was thoroughly mixed with 30 mg (15 wt %) of a EuCl$_3$ flux and sealed in an evacuated quartz tube. The ampoule was heated to 400° C. over 2 hours, dwelled for 1 hour at that temperature, and then was heated to 900° C. over 1.5 hours and dwelled at that temperature for 6 h before being slowly cooled to room temperature at 50° C./hr.

Example 22 EuAlGa$_{1.5}$S$_{4.75}$ (Sample Number ELTAlS-056E)

A 200 mg portion of the 1.2 g mixture of stoichiometric amounts of Eu, Al$_2$S$_3$, Ga$_2$S$_3$ and S prepared in Example 18 was thoroughly mixed with 30 mg (15 wt %) of a EuI$_2$ flux and sealed in an evacuated quartz tube. The ampoule was heated to 400° C. over 2 hours, dwelled for 1 hour at that temperature, and then was heated to 900° C. over 1.5 hours and dwelled at that temperature for 6 h before being slowly cooled to room temperature at 50° C./hr.

Example 23 Eu$_{0.97}$Gd$_{0.03}$Al$_{0.92}$Ga$_{1.38}$S$_{4.45}$ (Sample Number YBG-170424-2)

Stoichiometric amount of Eu, Al, Ga$_2$S$_3$, Gd$_2$O$_3$, S, and 5 wt % excess S were thoroughly ground in a mortar with a pestle in the glove box. The mixtures were placed in dried silica tubes, which were evacuated and sealed at a length of about 5 in. Reactions were carried out in a box furnace. The temperature was raised to 900° C. for 4 hours and held for 12 hours then cooled to room temperature for 6 hours.

Example 24 EuAl$_2$S$_4$ (Sample Number ELTAlS-006C), Comparative Example

A mixture of stoichiometric amounts of Eu, Al, S, and a few wt. % excess of S was thoroughly mixed under argon and sealed in an evacuated quartz tube. The ampoule was heated to 400° C. over 6 hours, dwelled for 6 hours at that temperature, and then was heated to 800° C. and dwelled at that temperature for 24 hours before being cooled to room temperature over 9 hours. The sample was thoroughly mixed under argon and sealed in an evacuated quartz tube. The heating step was repeated.

Example 25 EuAl$_{2.33}$S$_{4.28}$ (Sample Number ELTAlS-016C)

A mixture of stoichiometric amounts of Eu, Al, S, and a few wt. % excess of S was thoroughly mixed under argon and sealed in an evacuated quartz tube. The ampoule was heated to 400° C. over 6 hours, dwelled for 6 hours at that temperature, and then was heated to 800° C. and dwelled at that temperature for 24 hours before being cooled to room temperature over 6 hours. The sample was thoroughly mixed under argon and sealed in an evacuated quartz tube. The heating step was repeated.

Example 26 EuAl$_{2.7}$S$_{5.05}$ (Sample Number ELTAlS-016E)

A mixture of stoichiometric amounts of Eu, Al, S, and a few wt. % excess of S was thoroughly mixed under argon and sealed in an evacuated quartz tube. The ampoule was heated to 400° C. over 6 hours, dwelled for 6 hours at that temperature, and then was heated to 800° C. and dwelled at that temperature for 120 hours before being cooled to room temperature over 6 hours. The sample was thoroughly mixed under argon and sealed in an evacuated quartz tube. The heating step was repeated with the dwell step at 800° C. for 48 hours.

Example 27 EuAl$_{2.9}$S$_{5.35}$ (Sample Number ELTAlS-016F)

A mixture of stoichiometric amounts of Eu, Al, S, and a few wt. % excess of S was thoroughly mixed under argon and sealed in an evacuated quartz tube. The ampoule was heated to 400° C. over 6 hours, dwelled for 6 hours at that temperature, and then was heated to 800° C. and dwelled at that temperature for 48 hours before being cooled to room temperature over 6 hours. The sample was thoroughly mixed under argon and sealed in an evacuated quartz tube. The heating step was repeated.

Relative photoluminescent intensities were compared for EuAl$_2$S$_4$, EuAl$_{2.33}$S$_{4.28}$, EuAl$_{2.7}$S$_{5.05}$, and EuAl$_{2.9}$S$_{5.35}$ using 395 nm excitation. Setting EuAl$_2$S$_4$ as 100%, EuAl$_{2.33}$S$_{4.28}$ was more intense at 109%, EuAl$_{2.7}$S$_{5.05}$ was the most intense at 378% and $EuAl_{2.9}S_{5.35}$ was also more intense than the comparative example by 292%.

Example 28 $EuGa_2S_4$ (Sample Number ELTAlS-062A), Comparative Example

Stoichiometric amounts of Eu, $Ga_2S_3$ and S, with 20 wt % excess S were homogenized under argon. The mixture was combined with 136 mg (6 mg/cm$^3$) $I_2$ prior to sealing in an approx. 8 in evacuated quartz tube. The ampoule was placed in a horizontal tube furnace with a natural gradient and heated to 400° C. over 6 h, dwelled for 6 h, then heated to 900° C. over 2.5 h and dwelled for 72 h before being slowly cooled to room temperature over 24 h. The phosphor powder had a peak emission wavelength of 549 nm and a full width at half maximum of 43 nm when excited with 405 nm light from an LED.

Example 29 $EuGa_2S_4$ (Sample Number ELTAlS-062B), Comparative Example

Stoichiometric amounts of Eu, $Ga_2S_3$ and S, with 20 wt % excess S were homogenized under argon. The mixture was combined with 60 mg (15 wt %) $GaCl_3$ prior to sealing in an approx. 8 in evacuated quartz tube. The ampoule was placed in a horizontal tube furnace with a natural gradient and heated to 400° C. over 6 h, dwelled for 6 h, then heated to 900° C. over 2.5 h and dwelled for 72 h before being slowly cooled to room temperature over 24 h. The phosphor powder had a peak emission wavelength of 551 nm and a full width at half maximum of 39 nm when excited with 405 nm light from an LED.

Example 30 $EuGa_{2.7}S_{5.05}$ (Sample Number ELTAlS-063A)

Stoichiometric amounts of Eu, $Ga_2S_3$ and S, with 20 wt % excess S were homogenized under argon. The mixture was combined with 136 mg (6 mg/cm$^3$) $I_2$ prior to sealing in an approx. 8 in evacuated quartz tube. The ampoule was placed in a horizontal tube furnace with a natural gradient and heated to 400° C. over 6 h, dwelled for 6 h, then heated to 900° C. over 2.5 h and dwelled for 72 h before being slowly cooled to room temperature over 24 h. The phosphor powder had a peak emission wavelength of 549 nm and a full width at half maximum of 41 nm when excited with 405 nm light from an LED, and appeared visibly brighter than the comparative example 28.

Example 31 $EuGa_{2.7}S_{5.05}$ (Sample Number ELTAlS-063B)

Stoichiometric amounts of Eu, $Ga_2S_3$ and S, with 20 wt % excess S were homogenized under argon. The mixture was combined with 60 mg (15 wt %) $GaCl_3$ prior to sealing in an approx. 8 in evacuated quartz tube. The ampoule was placed in a horizontal tube furnace with a natural gradient and heated to 400° C. over 6 h, dwelled for 6 h, then heated to 900° C. over 2.5 h and dwelled for 72 h before being slowly cooled to room temperature over 24 h. The phosphor powder had a peak emission wavelength of 550 nm and a full width at half maximum of 39 nm when excited with 405 nm light from an LED, and appeared visibly brighter than the comparative example 29.

Phosphor Converted LED Examples

A phosphor slurry was created by combining 21.40 mg Dow Corning OE-6550 2 part silicone, 0.98 mg red phosphor, BR101J and 2.67 mg of a green phosphor of the present invention (example 5, $EuAl_{0.92}Ga_{1.38}S_{4.45}$, x=0.3). Phosphor converted LEDs 1-3 (examples 24-26 below) were fabricated using portions of this slurry, and vary from each other only in the amount of slurry deposited on the LED.

Example 32 Phosphor Converted LED 1

Figure 9:
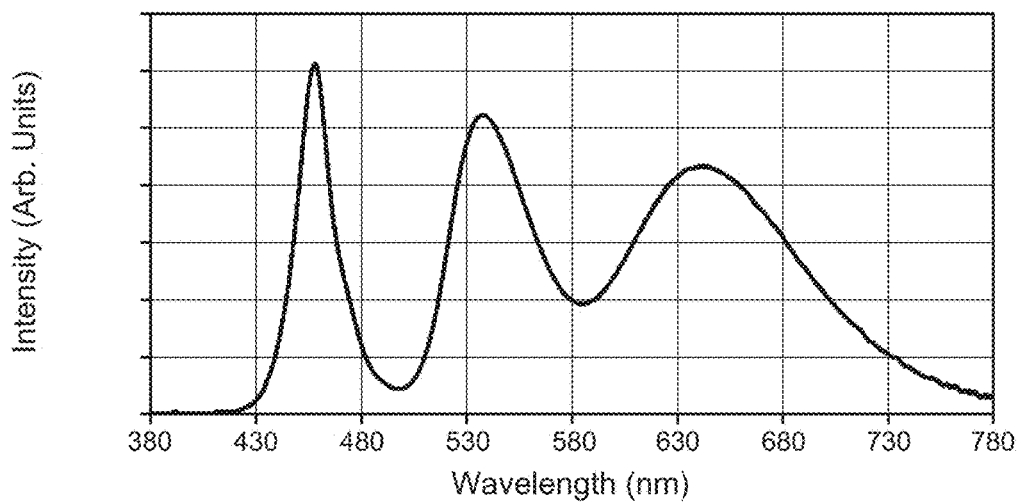
FIG. 9 shows an emission spectrum for an example phosphor converted LED.

The phosphor slurry described above was applied on top of a blue emitting InGaN based LED mounted in a 2835 PLCC package from Power Opto Co., and the silicone was cured overnight at ca. 100° C. The emission spectrum of this LED, shown in FIG. 9, was measured with an Ocean Optics spectrometer. The phosphor converted LED of this example was measured to have a correlated color temperature (CCT) of 4625K, a duv of 0.0046, and a CRI of 83, corresponding to a neutral white.

Example 33 Phosphor Converted LED 2

Figure 10:
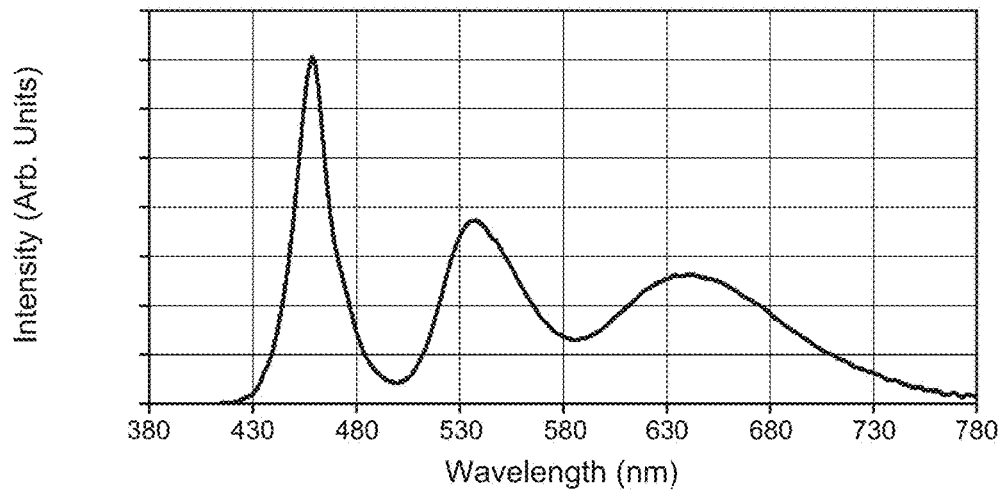
FIG. 10 shows an emission spectrum for another example phosphor converted LED.

The phosphor slurry described above was applied on top of a blue emitting InGaN based LED mounted in a 2835 PLCC package from Power Opto Co., and the silicone was cured overnight at ca. 100° C. The emission spectrum of this LED, shown in FIG. 10, was measured with an Ocean Optics spectrometer. The cured layer of slurry on the LED in this example was thinner than that in Example 25 (phosphor converted LED 1). The phosphor converted LED of this example was measured to have a correlated color temperature (CCT) of 6575K, a duv of 0.0045, and a CRI of 85, corresponding to a cool white.

Example 34 Phosphor Converted LED 3

Figure 11:
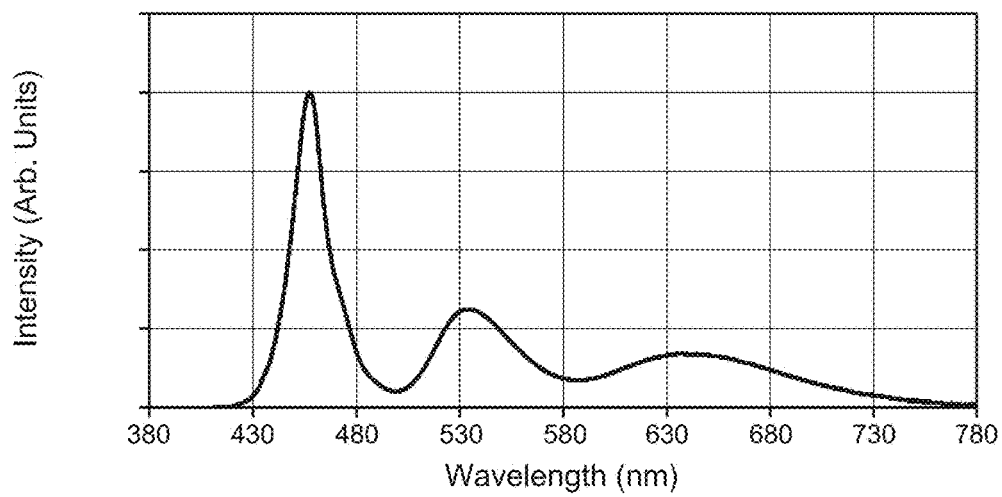
FIG. 11 shows an emission spectrum for another example phosphor converted LED.
Figure 12:
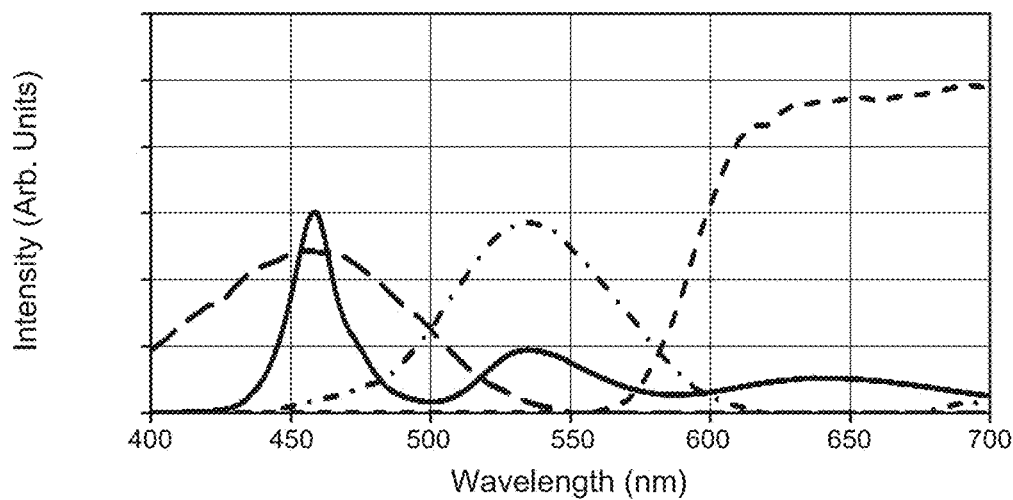
FIG. 12 shows the emission spectrum for the example phosphor converted LED of FIG. 11 overlaid with example color filters.

The phosphor slurry described above was applied on top of a blue emitting InGaN based LED mounted in a 2835 PLCC package from Power Opto Co., and the silicone was cured overnight at ca. 100° C. The emission spectrum of this LED, shown in FIG. 11, was measured with an Ocean Optics spectrometer. The cured layer of slurry on the LED in this example was thinner than that in Example 26 (phosphor converted LED 2). The phosphor converted LED of this example was measured to have CIE xy coordinates of 0.253, 0.250, suitable for backlighting applications. FIG. 12 shows the emission (solid line) from this phosphor converted LED overlaid with an example set of LCD color filters: blue (long dash), green (alternating dash and dot), and red (short dash). The emission spectrum is a good match for the example color filters shown in the figure.

Various embodiments are described in the following clauses.

Clause 1. A luminescent composition of matter characterized by the formula $REM_{2+x}E_y$, wherein:
RE is one or more rare earth elements;
M is one or more elements selected from the group Al, Ga, B, In, Sc, Lu, and Y;
E is one or more elements selected from the group S, Se, O, and Te;
x is greater than zero; and
y has the value that achieves charge balance in the formula assuming that E has a charge of −2.

Clause 2. The luminescent composition of matter of clause 1, wherein RE is Eu.

Clause 3. The luminescent composition of matter of clause 1, wherein RE comprises Eu and Gd.

Clause 4. The luminescent composition of matter of clause 1, having exclusively an $EuM_2E_4$. pseudoorthorhombic crystal structure.

Clause 5. The luminescent composition of matter of clause 1, having a mixture of predominantly an $EuM_2E_4$ pseudoorthorhombic crystal structure and one or more binary chalcogenide crystal structures.

Clause 6. The luminescent composition of matter of any of clauses 1-5, wherein the composition is characterized by the formula $Eu(Al_{0.4}Ga_{0.6})_{2+x}S_y$, where x is greater than zero.

Clause 7. The luminescent composition of matter of any of clauses 1-5, wherein:
M is Al; and
E is S, Se, or a mixture of S and Se.

Clause 8. The luminescent composition of matter of any of clauses 1-7, wherein x is greater than or equal to 0.5.

Clause 9. The luminescent composition of matter of any of clauses 1-8, wherein x is greater than or equal to 0.7.

Clause 10. The luminescent composition of matter of any of clauses 1-5, wherein the composition is characterized by the formula $EuAl_{1.08}Ga_{1.62}S_{5.05}$.

Clause 11. A light emitting device comprising a phosphor of any of clauses 1-10.

Clause 12. A phosphor converted light emitting diode comprising:
a light emitting diode emitting light over a first wavelength range; and
a phosphor of any of clauses 1-10 arranged to be excited by emission from the light emitting diode and in response emit light over a second wavelength range.

This disclosure is illustrative and not limiting. Further modifications will be apparent to one skilled in the art in light of this disclosure and are intended to fall within the scope of the appended claims.

TABLE 1

Summary of experimental examples compositions and spectral properties

| Example | Sample | Empirical Composition | Phases Observed in PXRD | Peak emission wavelength/ nm | FWHM/ nm |
|---|---|---|---|---|---|
| 1 | KB3-063-406 | $EuAl_{2.133}B_{0.567}S_{5.05}$ | $Eu(Al_{0.79}B_{0.21})_2S_4$ | 505 | 34 |
| 2 | KB3-059-399 | $EuAl_{2.322}Lu_{0.378}S_{5.05}$ | | 501 | 35 |
| 3 | KB3-125-488 | $EuAl_{0.8}Ga_{1.2}S_4$ $AlCl_3$ flux | $Eu(Ga_{0.6}Al_{0.4})_2S_4$ | 535 | 42 |
| 4 | KB3-125-489 | $EuAl_{0.84}Ga_{1.26}S_{4.15}$ $AlCl_3$ flux | $Eu(Ga_{0.6}Al_{0.4})_2S_4$ + $(Ga,Al)_2S_3$ | 534 | 43 |
| 5 | KB3-125-490 | $EuAl_{0.92}Ga_{1.38}S_{4.45}$ $AlCl_3$ flux | $Eu(Ga_{0.6}Al_{0.4})_2S_4$ + $(Ga,Al)_2S_3$ | 539 | 44 |
| 6 | KB3-125-491 | $EuAlGa_{1.5}S_{4.75}$ $AlCl_3$ flux | $Eu(Ga_{0.6}Al_{0.4})_2S_4$ + $(Ga,Al)_2S_3$ | 535 | 43 |
| 7 | KB3-126-492 | $EuAl_{1.08}Ga_{1.62}S_{5.05}$ $AlCl_3$ flux | $Eu(Ga_{0.6}Al_{0.4})_2S_4$ + $(Ga,Al)_2S_3$ | 535 | 43 |
| 8 | KB3-126-493 | $EuAl_{1.16}Ga_{1.74}S_{5.35}$ $AlCl_3$ flux | $Eu(Ga_{0.6}Al_{0.4})_2S_4$ + $(Ga,Al)_2S_3$ | 533 | 43 |
| 9 | KB3-132-506 | $EuAl_{1.08}Ga_{1.62}S_{5.05}$ $AlF_3$ flux | | 530 | 48 |
| 10 | KB3-133-507 | $EuAl_{0.8}Ga_{1.2}S_4$ $AlF_3$ flux | | 532 | 47 |
| 11 | YBG-170419-1 | $EuAl_2Se_4$ | $EuAl_2Se_4$ + $EuSe$ + $Al_{1.33}Se_2$ | 486 | 34 |
| 12 | YBG-170419-2 | $EuAl_{2.4}Se_{4.6}$ | $EuAl_2Se_4$ + $EuSe$ | 488 | 34 |
| 13 | YBG-170419-4 | $EuAl_{2.4}Se_{3.6}S$ | $EuAl_2Se_4$ + $EuSe$ | 496 | 37 |
| 14 | YBG-170419-5 | $EuAl_{2.7}Se_{5.05}$ | $EuAl_2Se_4$ | 488 | 33 |
| 15 | KB3-132-503 | $EuAl_{2.07}In_{0.23}S_{4.45}$ | | 508 | 31 |
| 16 | KB3-132-504 | $EuAl_{1.84}In_{0.46}S_{4.45}$ | | 511 | 37 |
| 17 | KB3-132-505 | $EuAl_{1.61}Ga_{0.23}In_{0.46}S_{4.45}$ | | 517 | 45 |
| 18 | ELTAlS-056A | $EuAlGa_{1.5}S_{4.75}$ $AlBr_3$ flux | $Eu(Ga_{0.6}Al_{0.4})_2S_4$ + $(Ga,Al)_2S_3$ | 533 | 43 |
| 19 | ELTAlS-056B | $EuAlGa_{1.5}S_{4.75}$ $GaBr_3$ flux | $Eu(Ga_{0.6}Al_{0.4})_2S_4$ + $(Ga,Al)_2S_3$ | 541 | 44 |
| 20 | ELTAlS-056C | $EuAlGa_{1.5}S_{4.75}$ $GaCl_3$ flux | $Eu(Ga_{0.6}Al_{0.4})_2S_4$ + $(Ga,Al)_2S_3$ | 541 | 45 |
| 21 | ELTAlS-056D | $EuAlGa_{1.5}S_{4.75}$ $EuCl_3$ flux | $Eu(Ga_{0.6}Al_{0.4})_2S_4$ + $(Ga,Al)_2S_3$ + $(Ga,Al)S$ | 537 | 44 |
| 22 | ELTAlS-056E | $EuAlGa_{1.5}S_{4.75}$ $EuI_2$ flux | $Eu(Ga_{0.6}Al_{0.4})_2S_4$ | 536 | 47 |
| 23 | YBG-170424-2 | $Eu_{0.97}Gd_{0.03}Al_{0.92}Ga_{1.38}S_{4.45}$ | $EuAl_{0.8}Ga_{1.2}S_4$ | 537 | 50 |
| 24 | ELTAlS-006C | $EuAl_2S_4$ | $EuAl_2S_4$ | 503 | 30 |
| 25 | ELTAlS-016C | $EuAl_{2.33}S_{4.28}$ | $EuAl_2S_4$ | 509 | 31 |
| 26 | ELTAlS-016E | $EuAl_{2.7}S_{5.05}$ | $EuAl_2S_4$ | 508 | 32 |
| 27 | ELTAlS-016F | $EuAl_{2.9}S_{5.35}$ | $EuAl_2S_4$ | 507 | 31 |
| 28 | ELTAlS-062A | $EuGa_2S_4$ $I_2$ flux | | 549 | 43 |
| 29 | ELTAlS-062B | $EuGa_2S_4$ $GaCl_3$ flux | | 551 | 39 |
| 30 | ELTAlS-063A | $EuGa_{2.7}S_{5.05}$ $I_2$ flux | | 549 | 41 |
| 31 | ELTAlS-063B | $EuGa_{2.7}S_{5.05}$ $GaCl_3$ flux | | 550 | 39 |

What is claimed is:

1. A luminescent composition of matter characterized by the formula $REM_{2+x}E_y$, wherein:
   RE is one or more rare earth elements;
   M is one or more elements selected from the group Al, Ga, B, In, Sc, Lu, and Y;
   E is one or more elements selected from the group S, Se, O, and Te;
   x is greater than or equal to 0.1 and less than or equal to 0.9; and
   y has the value that achieves charge balance in the formula assuming that E has a charge of −2.

2. The luminescent composition of matter of claim 1, wherein x is greater than or equal to 0.3.

3. The luminescent composition of matter of claim 1, wherein x is greater than or equal to 0.7.

4. The luminescent composition of matter of claim 1, having exclusively an $EuM_2E_4$ pseudoorthorhombic crystal structure.

5. The luminescent composition of matter of claim 1, having a mixture of predominantly an $EuM_2E_4$ pseudoorthorhombic crystal structure and one or more binary chalcogenide crystal structures.

6. The luminescent composition of matter of claim 1, wherein RE is Eu.

7. The luminescent composition of matter of claim 6, wherein x is greater than or equal to 0.3.

8. The luminescent composition of matter of claim 6, wherein x is greater than or equal to 0.7.

9. The luminescent composition of matter of claim 6, having exclusively an $EuM_2E_4$. pseudoorthorhombic crystal structure.

10. The luminescent composition of matter of claim 6, having a mixture of predominantly an $EuM_2E_4$ pseudoorthorhombic crystal structure and one or more binary chalcogenide crystal structures.

11. The luminescent composition of matter of claim 1, wherein RE comprises Eu and Gd.

12. The luminescent composition of matter of claim 11, wherein x is greater than or equal to 0.3.

13. The luminescent composition of matter of claim 11, wherein x is greater than or equal to 0.7.

14. The luminescent composition of matter of claim 1, wherein the composition is characterized by the formula $Eu(Al,Ga)_{2+x}S_y$.

15. The luminescent composition of matter of claim 14, wherein the ratio of Al to Ga is between about 1:3 and about 2:1.

16. The luminescent composition of matter of claim 14, wherein x is greater than or equal to 0.3.

17. The luminescent composition of matter of claim 14, wherein x is greater than or equal to 0.7.

18. The luminescent composition of matter of claim 14, having exclusively an $EuM_2E_4$. pseudoorthorhombic crystal structure.

19. The luminescent composition of matter of claim 14, having a mixture of predominantly an $EuM_2E_4$ pseudoorthorhombic crystal structure and one or more binary chalcogenide crystal structures.

20. The luminescent composition of matter of claim 17 wherein the composition is characterized by the formula $EuAl_{1.08}Ga_{1.02}S_{5.05}$.

21. The luminescent composition of matter of claim 1, wherein the composition is characterized by the formula $EuAl_{2+x}E_y$. where E is selected from the group S and Se.

22. The luminescent composition of matter of claim 21, wherein x is greater than or equal to 0.3.

23. The luminescent composition of matter of claim 21, wherein x is greater than or equal to 0.7.

24. The luminescent composition of matter of claim 21, having exclusively an $EuM_2E_4$. pseudoorthorhombic crystal structure.

25. The luminescent composition of matter of claim 21, having a mixture of predominantly an $EuM_2E_4$ pseudoorthorhombic crystal structure and one or more binary chalcogenide crystal structures.

26. The luminescent composition of matter of claim 21, wherein the composition is characterized by the formula $EuAl_{2.7}Se_{5.05}$.

27. The luminescent composition of matter of claim 21, wherein the composition is characterized by the formula $EuAl_{2.7}S_{5.05}$.

28. A light emitting device comprising:
   a light emitting diode emitting light over a first wavelength range; and
   a luminescent composition of matter arranged to be excited by emission from the light emitting diode and in response emit light over a second wavelength range;
   wherein the luminescent composition of matter is characterized by the formula $REM_{2+x}E_y$, wherein:
   RE is one or more rare earth elements;
   M is one or more elements selected from the group Al, Ga, B, In, Sc, Lu, and Y;
   E is one or more elements selected from the group S, Se, O, and Te;
   x is greater than or equal to zero and less than or equal to 0.9; and
   y has the value that achieves charge balance in the formula assuming that E has a charge of −2.

29. The light emitting device of claim 28, wherein RE is Eu and x is greater than or equal to 0.3.

30. The light emitting device of claim 28, wherein RE is Eu and x is greater than or equal to 0.7.

* * * * *